(12) United States Patent
Foertsch et al.

(10) Patent No.: US 9,532,705 B2
(45) Date of Patent: Jan. 3, 2017

(54) METHOD FOR CONTACT-FREE MAGNETIC NAVIGATION

(75) Inventors: Stefan Foertsch, Kunreuth (DE);
Henrik Keller, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1363 days.

(21) Appl. No.: 13/016,087

(22) Filed: Jan. 28, 2011

(65) Prior Publication Data

US 2011/0184240 A1    Jul. 28, 2011

(30) Foreign Application Priority Data

Jan. 28, 2010   (DE) .................. 10 2010 006 258

(51) Int. Cl.
*A61B 5/05* (2006.01)
*A61B 1/04* (2006.01)
*A61B 1/00* (2006.01)

(52) U.S. Cl.
CPC .......... *A61B 1/041* (2013.01); *A61B 1/00158* (2013.01); *A61B 34/73* (2016.02)

(58) Field of Classification Search
USPC .......... 600/103, 109, 117, 118, 160
See application file for complete search history.

(56) References Cited

U.S. PATENT DOCUMENTS

| | | | | |
|---|---|---|---|---|
| 4,564,363 A | * | 1/1986 | Bagnall et al. ............ | 604/891.1 |
| 5,681,260 A | * | 10/1997 | Ueda et al. ................ | 600/114 |
| 2003/0060702 A1 | | 3/2003 | Kuth et al. | |
| 2009/0112190 A1 | * | 4/2009 | Boyden et al. ............ | 604/891.1 |
| 2009/0318762 A1 | | 12/2009 | Segawa et al. | |

FOREIGN PATENT DOCUMENTS

| | | |
|---|---|---|
| DE | 101 61 958 A1 | 3/2003 |
| EP | 1 972 255 | 9/2008 |
| WO | WO 2010/034582 A1 | 4/2010 |

* cited by examiner

*Primary Examiner* — Ryan Henderson
*Assistant Examiner* — Aaron B Fairchild
(74) *Attorney, Agent, or Firm* — Schiff Hardin LLP

(57) ABSTRACT

In a method and a system for contact-free magnetic navigation of a magnetic body in a work space that is at least partially filled with a fluid, a thickening agent is added to the fluid. The use of a thickening agent as an additive for such a fluid is also described.

9 Claims, No Drawings

METHOD FOR CONTACT-FREE MAGNETIC NAVIGATION

BACKGROUND OF THE INVENTION

Field of the Invention

The present invention concerns a method and a system for contact-free magnetic navigation of a magnetic body in a work space that is filled at least partially with a fluid. The invention furthermore concerns the use of a thickening agent as an additive for such a fluid.

Description of the Prior Art

Methods and systems of the aforementioned type are used in the medical field. The magnetic body is in the form of an endoscopy capsule. A patient in a work space of the coil system is examined with this endoscopy capsule. In this work space (which is accessible from the outside) the magnetic forces of the coil system act on the magnetic body that is located in the patient and the part of the patient body is introduced into the work space of the coil system. The magnetic body (endoscopy capsule, capsule endoscope) constitutes a probe with which measurements (in particular image exposures) of internal organs of the patient can be made.

The endoscope capsule has a biocompatible housing containing at least one magnetic element for navigation by means of a magnetic field that can be generated by an external magnet system (coil system) and at least one sensor device to detect medically relevant data and/or at least one therapy device to administer a therapeutic agent.

Such an endoscopy capsule (which is also known as a capsule endoscope) is known from DE 101 42 253 C1 and from the corresponding US 2003/0060702 A1, and there is designated as an "endorobot".

The endorobot known from DE 101 42 253 C1 can be navigated in a hollow organ (for example the gastrointestinal tract) of a patient by means of a magnetic field that is generated by an external magnet system (coil system), i.e. a magnet system arranged outside of the patient. Changes of the orientation of the endorobot in the hollow organ of the patient can be detected and compensated automatically by an integrated system for orientation control that involves a position measurement of the endorobot and an automatic regulation of the magnetic field or the coil currents. Furthermore, the endorobot can be navigated in a targeted manner into desired regions of the hollow organ. This type of capsule endoscopy is therefore also designated as MGCE (Magnetically Guided Capsule Endoscopy).

In a gastroscopy (endoscopically implemented examination of the human or animal stomach) the endoscopy capsule is orally administered to the patient and arrives in the stomach via the esophagus. The expansion of the stomach that is conducted before the oral administration of the endoscopy capsule takes place by means of a fluid that is selectively administered into the stomach of the patient with a stomach probe, or is administered to the patient for independent consumption (drink solution).

During the gastroscopy different quantities, measurement values or samples are taken inside the stomach and provided to a physician or assistant for evaluation. For example, content substances or concentrations of the stomach contents are measured, the chemical composition of the gastric juices is determined or image data of the stomach mucosa are collected.

To transfer measurement and/or image data from the inside of the stomach, the endoscopy capsule is in communication (for example via a radio connection) with a transmission station that is in proximity to the patient. The endoscope capsule can be magnetically navigated accordingly for targeted acquisition of measurement and/or image data from specific regions of the stomach.

The housing of the endoscopy capsule is fashioned either in the shape of an ellipsoid or in the shape of a cylinder, for example. A cylindrical housing has a semi-spherical cap in at least one of its two face-side regions. Both face-side regions of the housing respective have a semi-spherical cap made of an optically transparent material. Such an endoscopy capsule can then respectively have an optical sensor device (CMOS camera or CCD chip, for example) at each of face-side regions.

If, in the MGCE, an endoscopy capsule swims in a fluid, the endoscopy capsule can then already be aligned in space by a relatively weak magnetic field and can be moved in the horizontal and vertical. Since the fluid is typically a normal water, a number of disadvantages are achieved.

Although vertical movement (diving) of the endoscopy capsule in the fluid is possible, there have previously existed no applicable solutions to let the endoscopy capsule float in an arbitrary position between the surface of the fluid and the base of the stomach. Although a manual regulation would be possible under specific requirements, a high image rate would be required in the acquisition of the image data. This can be realized only at a very high cost due to the necessary online transmission during the navigation.

Furthermore, due to physical effects caused by the magnetic forces the endoscopy capsule does not remain stable at a desired position at the fluid surface. The movements of the endoscopy capsule therefore must be manually corrected by the user, which requires a certain amount of practice. A possible solution for stabilization of an endoscopy capsule is a to generate what are known as peak fields, as described in the German Patent Application 10 2008 049 198.5, filed on 26 Sep. 2008. The strong magnetic fields generated by the peak fields can keep the endoscopy capsule stable in the horizontal plane. However, the power consumption increases significantly and only very limited vertical movements of the endoscopy capsule are possible.

Moreover, it can be that the forces exerted on the endoscopy capsule for an intended reverse movement of the endoscopy capsule are not sufficient for this movement since the tip of the endoscopy capsule projects from the fluid (water, for example) and thus the surface tension of the fluid must first be overcome. In order to achieve a solution in these cases, the endoscopy capsule is moistened at its tip with the aid of jerking movements and thus is more easily submerged. However, due to the high velocity with which these measures must be taken, this leads to unusable video images for short periods of time, so the operator of the magnetic coil system may possibly lose his or her orientation.

SUMMARY OF THE INVENTION

An object of the present invention is to provide a method with which a magnetic body can be navigated into a desired position in a work space in a simple manner and without contact.

The invention is furthermore has the object of specifying a system with which a magnetic body can be navigated into a desired position in a work space in a simple manner and without contact.

The method according to the invention serves for contact-free magnetic navigation of a magnetic body in a work space that is filled at least partially with a fluid, wherein according to the invention a thickening agent is added to the fluid.

The system according to the invention serves for the contact-free magnetic navigation of a magnetic body in a work space that is filled at least partially with a fluid, wherein according to the invention a thickening agent is added to the fluid.

In MGSE the magnetic body is fashioned as a magnetically navigable endoscopy capsule.

According to the invention, a higher density (and thus viscosity) of the fluid is imparted by the addition of a thickening agent to the fluid in which the magnetic body (endoscopy capsule, endoscopy capsule) swims.

DESCRIPTION OF THE PREFERRED EMBODIMENTS

By the use of a thickening agent as an additive for a fluid with which a work space is at least partially filled—wherein a magnetic body can be magnetically navigated in the work space—the density of the fluid (and therefore its viscosity) is increased, whereby the braking effect of the fluid on the magnetic body is correspondingly increased.

The braking effect that is exerted on the magnetic body in the fluid is directly proportional to the density or viscosity of the fluid. The correct dosing of the thickening agent allows the magnetic body to move vertically and allows the braking to be intensified so that the magnetic body can remain at an arbitrary vertical position. Even for the case that the dosing of the thickening agent in the fluid is not made precisely, the unwanted vertical movements would be slowed in terms of their velocity, such that the vertical movements of the endoscopy capsule can be manually corrected by the user.

Given the correct dosing of the thickening agent, the magnetic body is only slightly braked by the increased viscosity of the fluid. This slight braking is sufficient to eliminate unwanted movements of the magnetic body. The required forces for movements of the magnetic both therefore do increase slightly. The power consumption is only slightly affected by this. In comparison to peak fields, the increased power consumption is quite small, for example.

The higher density or the higher viscosity of the fluid ensures that the magnetic body can no longer pierce the surface of the fluid with the aid of its own buoyancy force. The negative effects of the surface tension thus no longer occur.

Given the solution according to the invention, the disadvantages known in the prior art are avoided or significantly reduced in that a thickening agent is added to the fluid.

The system according to the invention is preferably used in a medical apparatus. In the event that this is a magnetically guided capsule endoscopy (MGCE), the magnetic body (embodied as a probe) is fashioned as an endoscopy capsule.

In order to enable use of the method and the system according to the invention in a medical field, in a preferred embodiment the thickening agent is fashioned as a biocompatible thickening agent.

According to particularly advantageous embodiments, agar-agar, gelatins or polysaccharide (for example starch or pectin) are provided as a biocompatible thickening agent. All aforementioned thickening agents have a good compatibility for human digestion, wherein agar-agar is also suitable for vegetarians.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for contact-free magnetic navigation, comprising:
    a magnetic body configured for introduction in vivo into a workspace of a living subject that is at least partially filled with a fluid;
    a thickening agent added in vivo to said fluid that thickens said fluid to increase a braking effect that said fluid exerts on said magnetic body; and
    a magnet system that generates a magnetic field in said fluid thickened by said thickening agent with which said magnetic body interacts to navigate said magnetic body in vivo in said workspace in a contact-free manner.

2. A system as claimed in claim 1 wherein said thickening agent is a biocompatible thickening agent.

3. A system as claimed in claim 2 wherein said biocompatible thickening agent is agar-agar.

4. A system as claimed in claim 2 wherein said biocompatible thickening agent is gelatin.

5. A system as claimed in claim 2 wherein said biocompatible thickening agent is a polysaccharide.

6. A system as claimed in claim 2 wherein said polysaccharide is starch.

7. A system as claimed in claim 5 wherein said polysaccharide is pectin.

8. A medical apparatus comprising:
    a magnetic body comprising a probe, said magnetic body being configured for introduction in vivo into an organ of a patient, said organ being partially filled with fluid, and said probe being configured to implement a medical examination in said organ;
    a thickening agent added in vivo to said fluid that thickens said fluid to increase a braking effect that said fluid exerts on said magnetic body; and
    a magnetic navigation system that generates a magnetic field in said fluid thickened by said thickening agent that interacts with said magnetic body to navigate said magnetic body in said organ in a contact-free manner.

9. A medical apparatus as claimed in claim 8 wherein said probe is an endoscopy capsule.

\* \* \* \* \*